United States Patent [19]
Mendoza

[11] Patent Number: 5,374,189
[45] Date of Patent: Dec. 20, 1994

[54] INTEGRALLY FORMED DISPOSABLE PROPHY ANGLE AND DRIVE MECHANISM THEREFOR

[75] Inventor: Jose L. Mendoza, Rancho Cordova, Calif.

[73] Assignee: Denticator International, Inc., Sacramento, Calif.

[21] Appl. No.: 942,734

[22] Filed: Sep. 9, 1992

[51] Int. Cl.$^5$ .................................................. A61C 3/06
[52] U.S. Cl. ...................................... 433/125; 433/132
[58] Field of Search ........................ 433/125, 132, 166

[56] References Cited

U.S. PATENT DOCUMENTS

| | | | |
|---|---|---|---|
| Re. 24,391 | 11/1957 | McFadden | 433/132 |
| 263,814 | 9/1882 | Schmitz | 433/112 |
| 1,999,488 | 4/1935 | Swisher et al. | 433/128 |
| 2,025,779 | 12/1935 | Roelke | 433/128 |
| 2,135,933 | 11/1938 | Blair | 433/166 |
| 2,300,828 | 11/1942 | Goldenberg | 433/166 |
| 2,315,016 | 3/1943 | Shotton | 433/133 |
| 2,328,270 | 8/1943 | Greenberg | 433/128 |
| 2,937,444 | 5/1960 | Kern | 433/132 |
| 3,163,934 | 1/1965 | Wiseman | 433/125 |
| 3,192,922 | 7/1965 | Winkler | 433/132 |
| 3,229,369 | 1/1966 | Hoffmeister et al. | 433/126 |
| 3,421,224 | 1/1969 | Brehm et al. | 433/132 |
| 3,727,313 | 4/1973 | Graham | 433/125 |
| 3,740,853 | 6/1973 | Brahler | 433/124 |
| 3,855,704 | 12/1974 | Booth | 433/101 |
| 3,877,574 | 4/1975 | Killick | 433/132 |
| 3,955,284 | 5/1976 | Balson | 433/132 |
| 3,987,550 | 10/1976 | Danne et al. | 433/133 |
| 4,053,983 | 10/1977 | Flatland | 433/133 |
| 4,182,041 | 1/1980 | Girard | 433/115 |
| 4,248,589 | 2/1981 | Lewis | 433/80 |
| 4,259,071 | 3/1981 | Warden et al. | 433/166 |
| 4,266,933 | 5/1981 | Warden et al. | 433/82 |
| 4,365,956 | 12/1982 | Bailey | 433/115 |
| 4,693,871 | 9/1987 | Geller | 433/116 |
| 4,795,343 | 1/1989 | Choisser | 433/116 |
| 4,842,516 | 6/1989 | Choisser | 433/132 |
| 4,941,828 | 7/1990 | Kimura | 433/114 |
| 5,020,994 | 6/1991 | Huang | 433/126 |
| 5,028,233 | 7/1991 | Witherby | 433/125 |
| 5,040,978 | 8/1991 | Falcon et al. | 433/125 |
| 5,094,615 | 3/1992 | Bailey | 433/88 |
| 5,120,220 | 6/1992 | Butler | 433/125 |
| 5,156,547 | 10/1992 | Bailey | 433/125 |

FOREIGN PATENT DOCUMENTS

| | | | |
|---|---|---|---|
| 646193 | 6/1937 | Germany. | |
| 102433 | 5/1951 | New Zealand | 433/132 |
| 2209284 | 5/1989 | United Kingdom. | |

Primary Examiner—Cary E. O'Connor
Attorney, Agent, or Firm—Bernhard Kreten

[57] ABSTRACT

An integrally formed disposable dental hand piece drive mechanism and prophylaxis fitting which renders less likely cross-contamination of patients by providing an economic, sterile prophy angle which can be discarded after only one use. An output shaft is supported for rotation within a housing. The shaft has an output end which is configured to couple with any of a variety of working tools such as a dentifrice holding cup, a brush, or other dental instrumentality. The output shaft is stimulated into rotation by means of an air stream which is directed on a surface of the output shaft which is within the housing which supports the output shaft. Thus, air, directed to the output shaft via an inlet passage, impinges against the shaft causing rotation. Thereafter the air exits through an outlet passage. An end of the housing remote from the output shaft removably attaches to both a source of air and a duct to receive exiting air.

22 Claims, 4 Drawing Sheets

INTEGRALLY FORMED DISPOSABLE PROPHY ANGLE AND DRIVE MECHANISM THEREFOR

FIELD OF THE INVENTION

The invention generally relates to instrumentalities used for prophylaxis in dentistry. More specifically, the instant invention is directed to a disposable prophy angle having an integrally formed drive mechanism associated therewith.

BACKGROUND OF THE INVENTION

There is ongoing concern for contamination of dental patients with respect to certain viruses and diseases. It has been reported that some diseases can be transmitted through the normal program of dental prophylaxis. Consequently, greater attention has been directed towards medical tools, and especially dental tools which can economically be used only once and still be discarded.

One area which has heretofore evaded the attempt at disposability involved the handpiece that a dentist uses to drive certain working instrumentalities that come in contact with a person's teeth. For certain types of endeavors, such as tooth drilling, it is frequently required to use extremely high speed air mechanisms in excess of 500,000 revolutions per minute. One such company, Oral Safe has shown that it can manufacture such a device.

Frequently, however, certain other dental endeavors, more particularly involving dental hygiene, do not require such high rotation. In fact, for the purposes of a hygienist, rotation speeds less than 30,000 rpm are adequate for providing buffing, polishing and burring. To date, until the instant application, no instrumentality is known to exist capable of this lower speed rotation in which the output shaft is directly driven as an air turbine.

Accordingly, the instant invention provides a direct drive between an air current and an output shaft at one extremity of a disposable prophy angle. Heretofore, a traditional methodology by which a disposable prophy angle had been utilized involves attaching the disposable prophy angle to a hand piece via a chuck and collet assembly. An air motor is housed within the hand piece. One problem with such a technique involves subsequent need for sterilization of the hand piece housing and collet/chuck assembly within which the air motor is carried.

It is now recognized that the cost of autoclaving should be factored into any price comparison that is to be made between disposable and non-disposable instrumentalities used in the medical and dental environment. Moreover, since autoclaving necessitates down time for the sterilization process, multiple set of instruments (which are traditionally quite expensive) are required. This itself adds to the cost of using non-disposables. When the labor associated with autoclaving is also taken into account, it appears that disposables compare quite favorably both from a cost perspective and certainly from a hygienic perspective.

The following prior art reflects the state of the art of which applicant is aware and is included herewith to discharge applicant's acknowledged duty to disclose relevant prior art.

| INVENTOR | PATENT NO. | ISSUE DATE |
| --- | --- | --- |
| Schmitz | 263,814 | September, 1882 |
| Swisher et al | 1,999,488 | April, 1935 |
| Roelke | 2,025,779 | December, 1935 |
| Goldenberg | 2,300,828 | November, 1942 |
| Shotton | 2,315,016 | March, 1943 |
| Greenberg | 2,328,270 | July, 1943 |
| Wiseman | 3,163,934 | January, 1965 |
| Hoffmeister et al | 3,229,369 | January, 1966 |
| Graham | 3,727,313 | April, 1973 |
| Brahler | 3,740,853 | June, 1973 |
| Danne et al | 3,987,550 | October, 1976 |
| Flatland | 4,053,983 | October, 1977 |
| Girard | 4,182,041 | January, 1980 |
| Warden et al | 4,266,933 | May, 1981 |
| Huang | 5,020,994 | June, 1991 |
| Witherby | 5,028,233 | July, 1991 |
| Falcon et al | 5,040,978 | August, 1991 |
| Butler | 5,120,220 | June, 1992 |
| Fed. Republic of Germany | 646,193 | June, 1937 |
| Advertisement for Oralsafe Disposable Handpiece | Dentistry Today | August 1992 |

It is respectfully submitted that none of these prior art devices teach singly, nor render obvious when considered in any conceivable combination, the nexus of the instant invention as especially claimed hereinafter.

SUMMARY OF THE INVENTION

Accordingly, the instant invention provides a direct drive between an air current and an output shaft at one extremity of a disposable prophy angle. The instant invention resolved the problems delineated hereinabove by the provision of a disposable prophy angle integrally formed with the drive mechanism and suitably constructed such that after a single usage, disposal is economically justifiable.

In one form of the invention, a device is provided having a coupling means at one end for attachment to a source of air. At another end, an output shaft supporting the dental appliance is provided. The passageway extending between the two ends includes both an air intake passage for communication with the output shaft and an air exit passage for venting the air from the passageway. The instant invention eliminates a connecting shaft from this output shaft to the chuck and collet assembly, as well as coupling of the chuck to the motor. In fact the chuck and collet assembly are surplus since the air drives the output shaft directly. As the result, disposable, direct-drive prophy angles are economically feasible.

OBJECTS OF THE INVENTION

It is a primary object of the present invention to provide a novel and useful integrally formed disposable dental hand piece drive mechanism and prophylaxis fitting.

It is another object of the present invention to provide a device as characterized above which is extremely durable in use, relatively economical to fabricate and lends itself to mass production techniques.

A further object of the present invention is to provide a device as characterized above which is extremely aseptic to thwart the likelihood of cross-contamination by being sufficiently economical to also be disposable.

Viewed from a first vantage point it is the object of the present invention to provide a dental prophy angle and drive mechanism, comprising a housing having a first end and a second end, a hand grasping area on an exterior of the housing and intermediate the first and second ends, a hollow passageway within an interior of the housing, entrance and exit means on the first end of the housing to couple respectively with a source of air to enter the housing and exhaust air to exit the housing, a partition within the housing to sequester entering air from exiting air, and air contacting means supported in the second end including prophy support means extending outside the housing, the air contacting means including means to react to the air from the entrance means and divert this air to said exit means thereby imparting rotation to itself.

Viewed from a second vantage point it is the object of the present invention to provide an integrally formed disposable dental handpiece drive mechanism and prophylaxis fitting, comprising a housing having a first end and a second end, an air coupling means at the first end, the second end of the housing supporting an output shaft emanating therefrom including means for attaching to said prophylaxis fitting, an output shaft including air reactive means contained within the housing and in direct communication with air admitted by the air coupling means, whereby the output shaft is directly driven by air impinging thereagainst.

Viewed from a third vantage point it is the object of the present invention to provide a method for rotating a prophylaxis instrument at speeds less than 50,000 rpm, the steps including forming a housing with a first end and a second end, configuring the housing with an interior partition extending from the first end to the second end, thereby defining an inlet flow path and an outlet flow path, coupling inlet fluid to the inlet flow path and an outlet fluid receiver to the outlet flow path, supporting and positioning a fluid responsive member in the second end of the housing to contact the inlet fluid and direct the fluid to the outlet flow path while reacting to the fluid flow by rotating, and utilizing the rotation of the fluid responsive member by coupling this fluid responsive member to an output device.

These and other objects will be made manifest when considering the following detailed specification when taken in conjunction with the appended drawing figures.

DESCRIPTION OF PREFERRED EMBODIMENTS

Considering the drawings now, wherein like reference numerals denote like parts throughout the various drawing figures, reference numeral 10 is directed to the integrally formed device including a disposable dental hand piece drive mechanism and prophylaxis fitting. In essence, the tool or device 10 includes a housing 15 having a first end or tail 20 and a second end or head 40. The housing 15 interposed between the first and second ends. The first end 20 includes an inlet 22 and an outlet 32. An interior of the device 10 includes a partition 30 which separates the fluid passing from the inlet to the outlet as the fluid travels within the housing 15. The fluid air travels from the inlet 22 along arrow "B", contacts the second end or head 40 and causes an output shaft 42 to rotate along arrow "C" in response to impingement by the air. Thereafter, the air is diverted away from output shaft 42 along arrow "D" to an outlet 32 contained at the tail 20.

Figure 1:
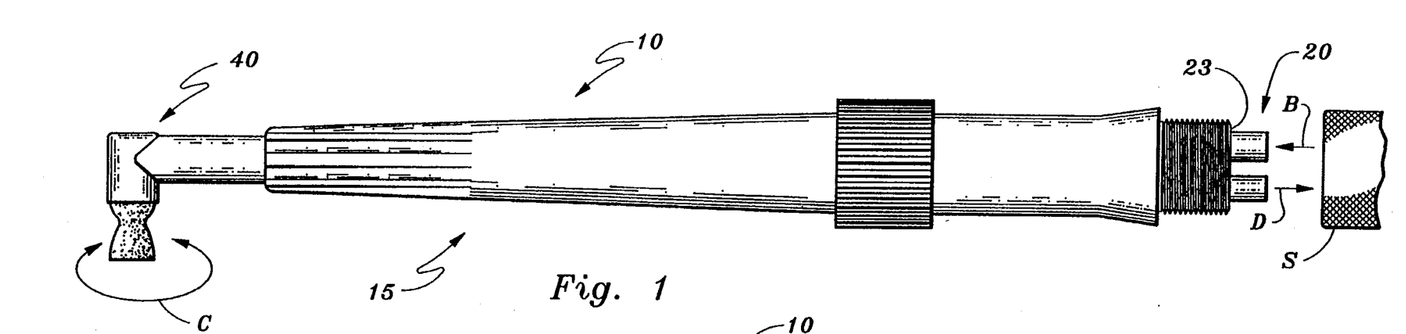
FIG. 1 is a side view of the apparatus according to the present invention in one form.
Figure 2:
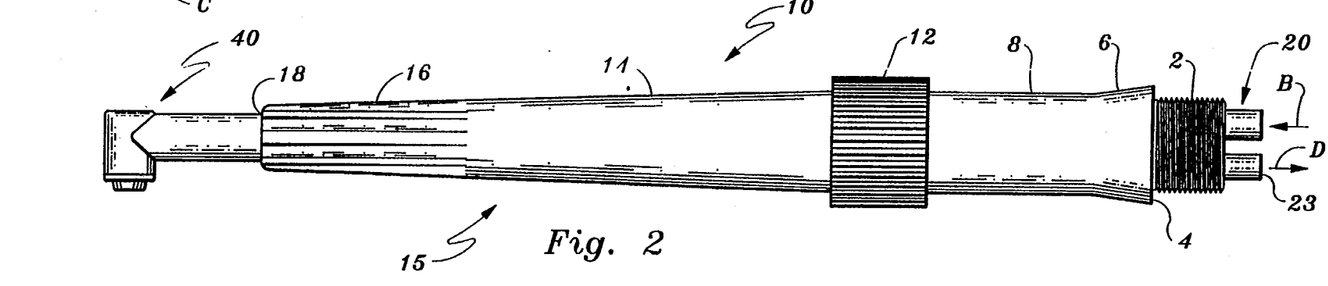
FIG. 2 is view similar to FIG. 1 with one of the components removed for added clarity.
Figure 3:
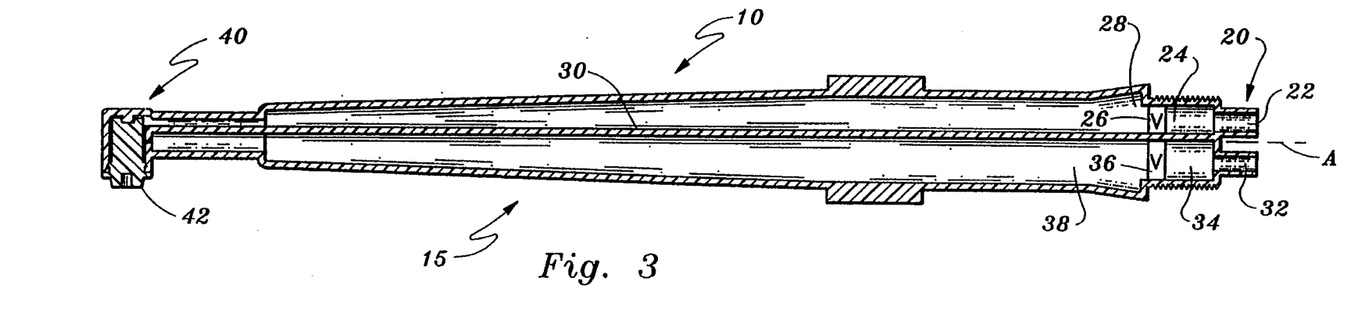
FIG. 3 is a sectional view similar to FIGS. 1 and 2 but taken along, a longitudinal center line in the plane of the paper.

More specifically, and with specific attention to FIGS. 1 through 3, it can be shown that the housing 15 includes adjacent its first end 20 a multiplicity of threads which circumscribe a substantially cylindrical section 2 for threaded coupling engagement with a source of air S. The source of air S also has means provided therewithin to remove air which exits from the tool 10 in a manner that shall become evident.

Immediately upstream from tail 20 (i.e. towards the head 40) a step 4 extends radially outwardly and transverse to a long axis "A", to provide an abutment between the threaded cylindrical section and a conical flare 6 which serves as a major transition towards the central portion of the housing 15. Flare 6 tapers towards the head 40. The conical flare 6 thereafter transitions to a more gentle taper 8. Taper 8 is immediately followed by a purchase area 12 of substantially cylindrical configuration. Purchase area 12 has a multiplicity of ridges extending parallel to the long axis "A" to facilitate the threading of the air source to the cylinder's threads 2 on the first end 20. Cylinder 2 includes an end wall 23 remote from step 4.

Immediately upstream from the purchase area 12, a palm support 14 is provided with a gentle incline which tapers towards the head 40 of the device 10. Knurling 16, also disposed on the incline, further transitions to a radially inwardly extending step 18 at an end of the housing 15 which is adjacent the head. The purpose of the knurling is to provide a beneficial tactile enhancement to prevent tool slippage in the hand of a dentist or other dental practitioner especially when manipulating the tool in and around the mouth area of a patient and in the presence of saliva.

Attention is now directed to FIG. 3 which shows a transverse sectional view of the housing. More specifically, the tail 20 includes a tubular air inlet 22 mounted on end wall 23 (FIG. 2). Inlet 22 allows air from the source S (FIG. 1) to enter into the device 10 along arrow "B". The air enters into the interior of the housing 15 by first residing within an interior of the threaded cylindrical section 2 defined by a first stage expansion chamber 24. To a certain extent this allows slowing of the air flow from the air inlet 22 because of the increase in cross-section in the chamber 24 compared to the inlet 22.

It may be that the air pressure that is routinely available in a dental operatory should be conveniently decreased without undue manipulation (and "down time") by the dental practitioner in order to realize a rotation of less than 30,000 rpm. It is to be noted that air sources commonly provided in a dental operatory can induce tool rotation 10–15 times greater than needed for the present purpose. One other way of achieving this decrease in addition to (or in lieu of) the first stage expansion chamber 24 is to place a regulator valve 26 strategically within the housing so that air will pass beyond the regulator valve 26 only at a desired downstream pressure. The regulator valve 26 is also optional and is shown as being positioned at the transition between the first stage expansion chamber 24 and an area denoted by reference numeral 28 which is generally described as an inlet passage.

As shown (relative to FIG. 3), the inlet passage 28 is segregated and sequestered to only an upper half of the device 10 by means of a partition 30 which extends along the entire length of the housing 15, from the tail 20 to the head 40. Air moves along arrow "B" from the first stage expansion chamber 24 into the inlet passage 28. The air flow rate can thus be further reduced by the expanded volume associated with the inlet passage 28. Ultimately, in a manner to be described, the air in this inlet passage 28 contacts a turbine 44 (FIG. 4) at the device's head 40.

Thereafter air exits in an opposite direction along arrow "D" and through the outlet passage 38 which is provided on a lower half of the housing 15, on a side of the partition 30 opposite the inlet passage 28. Optionally, the outlet passage 38 may communicate on its way to the air outlet 32 with another valve 36 and a back pressure chamber 34 on its way to the substantially cylindrical air outlet 32 which is supported in end wall 23. The purpose for the valve 36 and the back pressure chamber 34 is to provide the desired air resistance in the event that the inlet pressure is excessively high for the practitioner's needs and requires further modulation. By providing this impediment on the outlet side, the air flow through the device 10 may be capable of more precise control.

Attention is now directed to FIGS. 4 through 8 which show various details of the head generally depicted in the earlier drawing figures as reference numeral 40. As mentioned, the head 40 includes an output shaft 42 adapted to rotate about the direction of the arrow "C" in response to air flow which passes though the inlet passage 28 along arrow "B" via access opening 29. Air passing though the outlet passage 38 exits from port 39 in accordance with the arrow "D", shown in FIG. 4. The output shaft 42 is operatively coupled to a turbine body 44. The turbine body 44 includes a plurality of vanes 46 having a wide vane portion 46a at a "top" (i.e. adjacent the inlet passage 28); and a narrow vane portion 46b adjacent the outlet passage 38. As should now be evident, air impinging on the vanes imparts rotation to output shaft 42 along arrow "C" so that work can be done.

Figure 4:
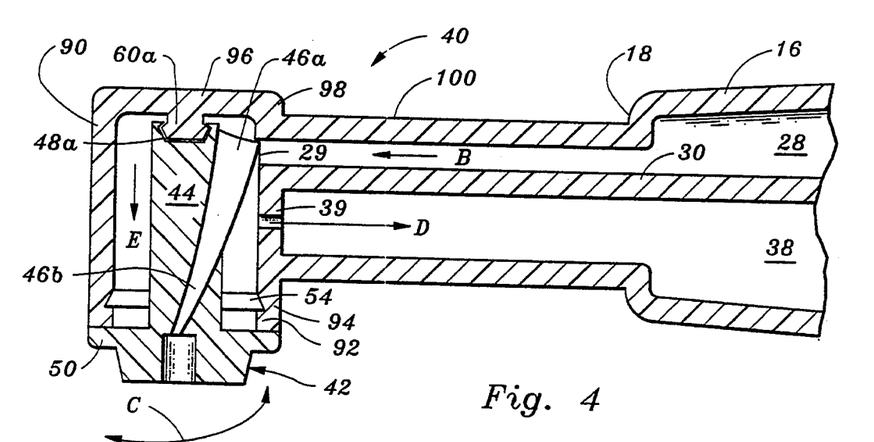
FIG. 4 is a detailed sectional view of one end shown in FIG. 3, the head
Figure 5:
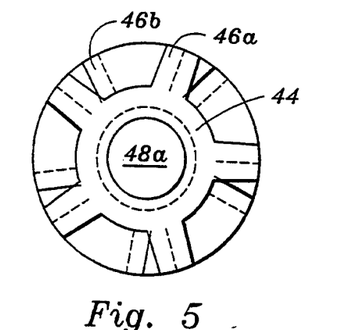
FIG. 5 is a top plan view of a turbine associated with the head or FIG. 4
Figure 6:
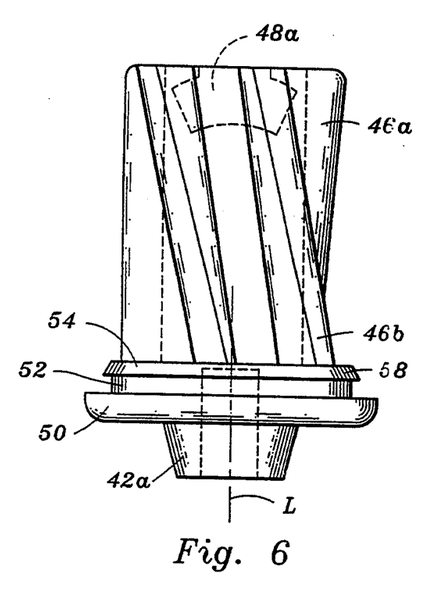
FIG. 6 is a side view of FIG. 5.

A top portion of the turbine body 44 includes a socket 48a to receive a spindle 60a therewithin. In one form of the invention as shown in FIGS. 4, 5 and 6, the socket 48a has a somewhat "keystone" shaped configuration when taken in section. That is, the socket 48a includes an arcuate bottom wall and an outwardly diverging truncated, conical side wall. The curved side wall terminates in an upwardly and inwardly directed vaulted wall portion which is also a truncated cone that terminates ultimately in a vertically oriented annular wall portion communicating with a top surface of the turbine body 44. Thus, this socket 48a is especially adapted for receiving a locking type bearing spindle, such as that shown at 60a, having a bulbous contour 60a complemental to the contour of the socket 48a. In other words, a ball and socket fitting is described which allows rotation about arrow "C".

More specifically, the bearing spindle 60a has an annular stem portion complemental to the annular wall portion of the turbine. The spindle includes a downwardly and outwardly diverging conical wall terminating in an inwardly and downwardly converging conical wall and concludes with a flat bottom surface.

Figure 7:
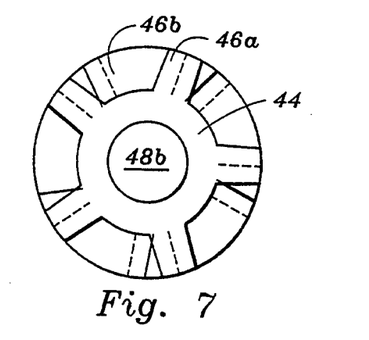
FIG. 7 is a top plan view as an alternative to that which is shown in FIG. 5.
Figure 8:
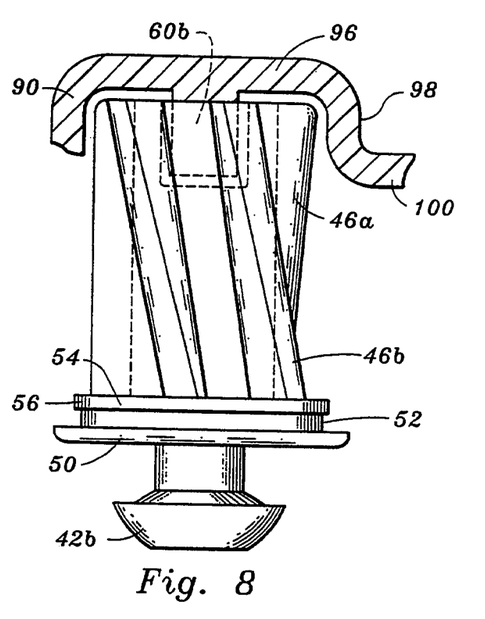
FIG. 8 is a side view alternative to that which is shown in FIG. 6.

FIGS. 7 and 8 show another version in which the socket 48b is in essence a cylindrical blind bore and the bearing spindle 60b is a substantially cylindrical projection nesting therewithin. In both cases, the purpose of the spindle is to retard precession of the turbine body 44. With respect to the first version 48a, 60a, a snap fit is provided which also is intended to preclude axial migration of the turbine body 44 in a downward sense along arrow "E" (with respect to FIG. 4).

Additional structure is provided to also retard the unwanted axial migration of the turbine body 44 away from the head 40. Again referring to FIGS. 4 through 8, each variation of output shaft 42 is provided with a turbine cap 50 intended to abut against or near a bottommost surface of the head 40. The turbine cap 50 is integrally formed with the turbine body 44. Just above the cap 50, an annular groove 52 is provided and formed in the turbine body. A locking ring 54 is formed above the groove 52. Collectively, the locking ring 54, annular groove 52 and turbine cap 50 locate and fix the turbine body 44 within the head 40 in a manner to be defined.

Note in FIG. 8 the locking ring 54 includes an outer profile 56 which is substantially square in section. On the other hand, in FIG. 6, the locking ring 54 may have an outer periphery 58 configured as a barb. That is, the barb 58 appears mitered with a sharpened edge adjacent the groove 52. This allows the turbine body 44 to be more easily inserted within the head 40 (opposite arrow "E") by elastically deforming the associated structure in the head. This renders subsequent removal of the turbine body 44 from the head much more difficult.

As shown in FIG. 6, one form of output shaft 42 is shown. This shaft 42a includes a cylindrical threaded bore coincident with the vertical longitudinal axis L of the turbine body 44. The output shaft 42a supports the threaded bore within a truncated conical outer contour such that the taper of the cone converges downwardly, away from the turbine body 44. FIG. 8 shows another version of output shaft 42b in which an inverted mushroom shaped boss 42b has been provided. The threaded shaft version of FIG. 6 lends itself to threaded connection with tools such as a threaded brush or burring tool as suggested in FIG. 9 while the mushroom shaped boss 42b lends itself for connection with a cup shaped prophy appliance, as suggested in FIG. 10. Two versions of prophy cup are detailed in FIGS. 11 and 12.

Figure 11:
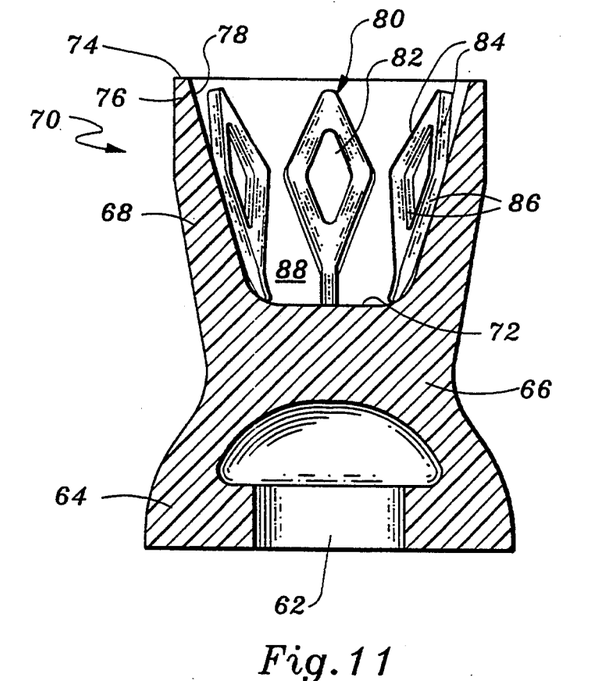
FIG. 11 is a sectional view of a prophy cup for use with the device.

Referring specifically to FIG. 11, the prophy cup 70 includes a recess 62 which is complemental to the mushroom shaped boss 42b which is to frictionally reside therewithin. The cup has a lower body portion 64 within which the recess 62 is provided. The cup 70 has a waist portion 66 extending up front body portion 64 front which flares upwardly and outwardly the walls 68 of the cup 70. FIG. 11 is taken in section to reflect interior details within the cup formed by the wall 68.

Figure 12:
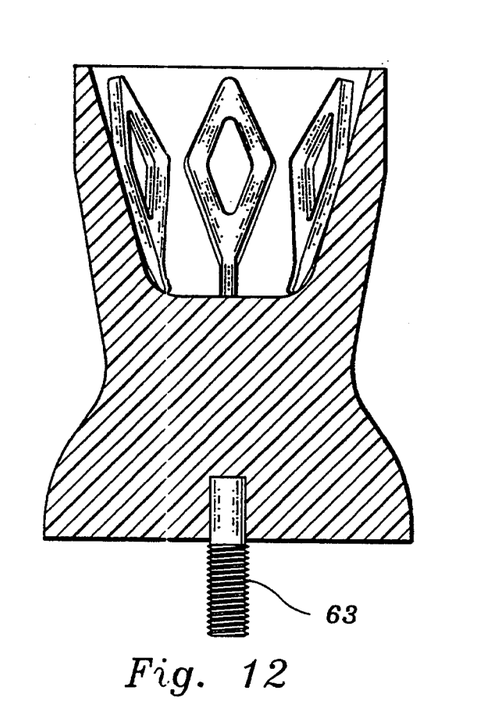
FIG. 12 is a sectional view of an alternative to that which is shown in FIG. 11.

As shown, the wall 68 has a thickened lower portion adjacent a base portion 72 on an interior of the cup 70. The exterior side walls 78 of the cup adjacent a lip 74 are substantially vertical, but interior wall 78 diverges outwardly on an inner portion of the cup. The interior wall 78 supports diamond-shaped retention means 80. The retention means 80 includes a central section 82 bounded on four sides by two upper short ribs 84 and two lower longer ribs 86 thereby forming the diamond-shaped configuration. A plurality of these diamond-shaped retention means 80 circumscribe the interior wall of the cup-shaped prophy 70 so that regions 88 between lower ribs 86 of the diamond shaped retention means 80 are also bounded by portions of the diamond-shaped retention means. The purpose of the structure thus far delineated is to assist in holding dentifrice or other forms of dental paste within the cup more reliably than is known in the prior art. Moreover, the ribs provide a scrubbing effect in the hygienic process. Rotation of the cup sometimes urges the dentifrice or paste to yield to centrifugal force and migrate out of the cup rather than reside on the cup until its intended placement on a person's teeth. The ribs 84, 86 define projections on an interior of the cup to hold the dentifrice. The salient difference between FIGS. 12 and 11 shows FIG. 12 has a threaded stem 63 in place of recess 62.

Referring back to FIG. 4, further details of the head 40 are shown. More specifically, the head includes a cylinder 90 which circumscribes the turbine body 44 and is spaced therefrom. The cylinder 90 includes a disc-shaped top wall 96 integrally formed with the cylinder 90. The spindle 60 depends from the disc-shaped top wall 96. A lower bottommost portion of the cylinder 90 includes an interior annular lip 92. Just above the annular lip 92, an annular recess 94 is provided. The lip 92 and recess 94 coact with the groove 52 and locking ring 54 of the turbine to retain the turbine.

Part of the cylinder 90 is seen partially occluding the outlet passageway 38. There is not total sealing of the opening, but at most a mere restriction defining port 39. As shown in FIG. 4, there is no impediment to the fluid flow along arrow "B" in the inlet passage 28 along access opening 29. Note that the transition 98 between the top wall 96 and the cylinder 90 is radiused. The transition 98 provides a step similar to step 18. A shank 100 extends between the transition 98 and the step 18. Shank 100 is substantially cylindrical and forms part of the housing and passages 28 and 38. Shank 100 also supports part of partition 30.

Figure 9:
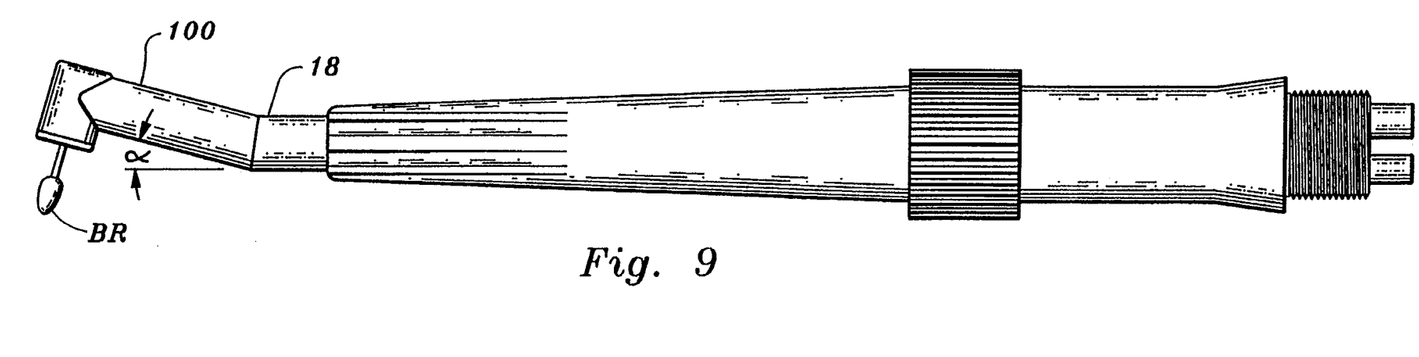
FIG. 9 is a side view similar to FIG. 1 as an alternative.
Figure 10:
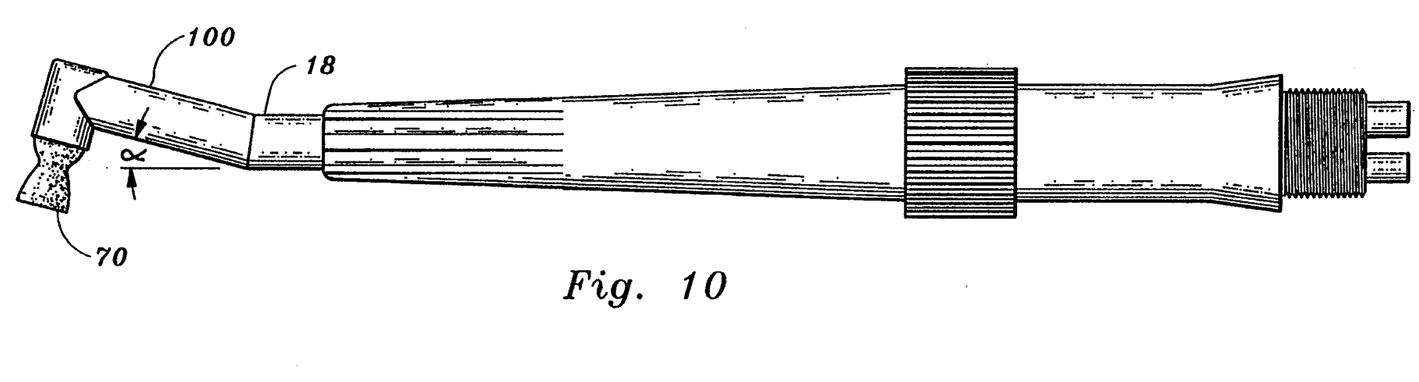
FIG. 10 is a side view of that which is shown in FIG. 9 as an alternative.

Referring now to FIGS. 9 and 10, a variation from that which is shown in the earlier drawing figures can now be explored. These versions are known as "contra angle" hand pieces and prophies. In this version, the shank 100 is skewed at an angle α with respect to its connection at the step 18. Typically, the angle α is a matter of design choice, but it is preferably 30°. Also as mentioned above, one version shows the prophy 70 (FIG. 10) while the FIG. 9 version shows a brush or bur BR.

In use and operation, the device is molded perhaps from a material such as plastic. It is to be noted that there are only three components. The prophy 70 or brush or bur BR is one component, the turbine structure is a second component with the remaining component or housing defines the third. The device is assembled so that turbine 44 is placed within the housing (opposite arrow "E") and the appropriate working head, whether the prophy, the brush, or a bur is disposed thereon. Next, air is coupled to the threaded end 2 and the device is ready for use.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A disposable dental prophy angle and drive mechanism, comprising, in combination:

a plastic housing having a first end and a second end, a hand grasping area on an exterior of said housing and intermediate said first and second ends, a hollow passageway within an interior of said housing, entrance and exit means on said first end of said housing to couple respectively with a source of air to enter said housing and exhaust air to exit said housing, a partition within said housing to sequester entering air from exiting air, and air contacting means supported in said second end including prophy support means extending outside said housing, said air contacting means including means to react to the air from said entrance means and divert this air to said exit means while imparting rotation to itself and, wherein said air contacting means includes a means to retain said air contacting means within said second end of said housing, said retention means including two complementally formed attachments including an annular ring and a complementally formed annular groove, one of said attachments formed on an interior of said second end of said housing and another of said attachments formed on an exterior surface of said air contacting means.

2. The device of claim 1 wherein said air contacting means is configured as a turbine having a body and a plurality of vanes disposed on an exterior side surface of said turbine body, and includes means for supporting said turbine in said second end.

3. A dental prophy angle and drive mechanism, comprising, in combination:

a housing having a first end and a second end, a hand grasping area on an exterior of said housing and intermediate said first and second ends, a hollow passageway within an interior of said housing, entrance and exit means on said first end of said housing to couple respectively with a source of air to enter said housing and exhaust air to exit said housing, a partition within said housing to sequester entering air from exiting air, and air contacting means supported in said second end including prophy support means extending outside said housing, said air contacting means including means to react to the air from said entrance means and divert this air to said exit means while imparting rotation to itself, and wherein said air contacting means is configured as a turbine having a body and a plurality of vanes disposed on an exterior side surface of said turbine body, and includes means for supporting said turbine in said second end, and wherein said turbine support means includes a socket on a top surface of said turbine and an annular groove on said side surface of said turbine, and said second end of said housing includes a complementally formed spindle for contact with said socket and said second end includes an annular lip for riding within said annular groove of said turbine to retain said turbine in said second end.

4. The device of claim 3 wherein said vanes on said turbine have an enlarged upper portion and a narrow lower portion and said enlarged upper portion is oriented to remain in registry with inlet air which has entered said housing, said narrow vane portion in registry with air exiting said housing.

5. The device of claim 4 wherein said first end includes a threaded cylindrical portion for operative coupling to the source of air and the source of air also operatively couples to both a tubular air inlet and a tubular air outlet on said first end, said inlet and outlet supported on an end wall of said threaded cylinder, said air inlet defining said entrance means which communicates with an inlet passageway formed by a portion of said housing and said partition, and said air outlet communicates with an outlet passageway formed by said partition and a remainder of said housing.

6. The device of claim 5 wherein said housing includes a step adjacent said threaded cylinder, a conical flare tapering towards said second end and in immediate communication with said step, a taper communicating with said flare having a less severe degree of taper than said flare, a purchase area communicating with said taper having a plurality of ridges disposed thereon to facilitate grasping said housing especially when operatively coupling said air source thereto, a palm support area connected to said purchase area, a knurled portion communicating with said palm support area, a step communicating with said knurling, a shank communicating with said step, a transition communicating with said shank, said shank communicating with said second end, and said second end defining a head, said head including a cylindrical wall transitioning into said shank at said transition, a disc-shaped top wall communicating with and sealing a top portion of said cylinder and an open bottom wall for reception therein of said turbine body.

7. The device of claim 6 wherein said shank is skewed from a long axis of said housing by an angle α.

8. The device of claim 5 wherein said hollow passageway within said housing in conjunction with said partition includes:

a first stage expansion chamber immediately downstream from said air inlet, a regulator valve in communication with said expansion chamber and downstream therefrom, an inlet passage downstream from said regulator valve, an access opening communicating with said turbine, a port receiving exiting air from said turbine, an outlet passage communicating with said port extending towards said air outlet, and back pressure means interposed between said outlet and said outlet passage.

9. The device of claim 5 wherein said turbine includes an output shaft having a mushroom shaped boss, and a prophy is frictionally engaged by said mushroom shaped boss, said prophy cup including a cup interior provided with a diamond-shaved retention means on an interior surface of said cup to retain dentifrice therein.

10. An integrally formed disposable dental handpiece drive mechanism and prophylaxis fitting, comprising, in combination:

a plastic housing having a first end and a second end, a partition within said housing, said partition bisecting said housing interior into an air exit means and an air entrance means, an air coupling means at said first end, said second end of said housing supporting an output shaft emanating therefrom including means for attaching to said prophylaxis fitting, a means to retain said output shaft within said second end of said housing, said retention means including two complementally formed attachments including an annular ring and a complementally formed annular groove, one of said attachments formed on an interior of said second end of said housing and another of said attachments formed on an exterior surface of said output shaft, said output shaft including air reactive means contained within said housing and in direct communication with air admitted by said air coupling means, whereby said output shaft is directly driven by air impinging thereagainst.

11. The device of claim 10 wherein said air reactive means includes a turbine having a body and a plurality of vanes disposed on an exterior side surface of said turbine body, and includes means for supporting said turbine in said second end.

12. An integrally formed disposable dental handpiece drive mechanism and prophylaxis fitting, comprising, in combination:

a housing having a first end and a second end, an air coupling means at said first end, said second end of said housing supporting an output shaft emanating therefrom including means for attaching to said prophylaxis fitting, said output shaft including air reactive means contained within said housing and in direct communication with air admitted by said air coupling means, whereby said output shaft is directly driven by air impinging thereagainst, and wherein said air reactive means includes a turbine having a body and a plurality of vanes disposed on an exterior side surface of said turbine body, and includes means for supporting said turbine in said second end, and wherein said turbine support means includes a socket on a top surface of said turbine and an annular groove on said side surface of said turbine, and said second end of said housing includes a complementally formed spindle for contact with said socket and said second end includes an annular lip for riding within said annular groove of said turbine to retain said turbine in said second end.

13. The device of claim 12 wherein said vanes on said turbine have an enlarged upper portion and a narrow lower portion and said enlarged upper portion is oriented to remain in registry with inlet air which has entered said housing, said narrow vane portion in registry with air exiting said housing.

14. The device of claim 13 wherein said first end includes a threaded cylindrical portion for operative coupling to the source of air and the source of air also operatively couples to both a tubular air inlet and a tubular air outlet on said first end, said inlet and outlet supported on an end wall of said threaded cylinder, said air inlet defining said entrance means which communicates with an inlet passageway formed by a portion of said housing and said partition, and said air outlet communicates with an outlet passageway formed by said partition and a remainder of said housing.

15. A method for rotating a disposable prophylaxis instrument at speeds less than 50,000 rpm, the steps including;

forming a housing from plastic material with a first end and a second end, configuring the housing with an interior partition extending from the first end to the second end, thereby defining an inlet flow path and an outlet flow path, coupling inlet fluid to the inlet flow path and an outlet fluid receiver to the outlet flow path, supporting and positioning a fluid responsive member in the second end of the housing to contact the inlet fluid and direct the fluid to the outlet flow path while reacting to the fluid flow by rotating, securing the fluid responsive member by providing a means to retain the fluid responsive member within the second end of the housing, the retention means including two complementally formed attachments including an annular ring and a complementally formed annular groove, one of said attachments formed on an interior of said second end of said housing and another of said attachments formed on an exterior surface of said fluid responsive member, and utilizing the rotation of the fluid responsive member by coupling this fluid responsive member to an output device.

16. The method of claim 15 including forming an output device as a cup member having a first and second recess, coupling the first recess adapted to the fluid responsive member and forming the second recess with a plurality of diamond-shaped retention means on an interior surface thereof, and placing dentifrice in the cup, rotating the fluid responsive member and applying the dentifrice to teeth of a person.

17. A method for rotating a prophylaxis instrument at speeds less than 50,000 rpm, the steps including;

forming a housing with a first end and a second end, configuring the housing with an interior partition extending from the first end to the second end, thereby defining an inlet flow path and an outlet flow path, coupling inlet fluid to the inlet flow path and an outlet fluid receiver to the outlet flow path, supporting and positioning a fluid responsive member in the second end of the housing to contact the inlet fluid and direct the fluid to the outlet flow path while reacting to the fluid flow by rotating, and utilizing the rotation of the fluid responsive member by coupling this fluid responsive member to an output device, and including forming an output device as a cup member having a first and second recess, coupling the first recess adapted to the fluid responsive member and forming the second recess with a plurality of diamond-shaped retention means on an interior surface thereof, and placing dentifrice in the cup, rotating the fluid responsive member and applying the dentifrice to teeth of a person, and including supporting the fluid responsive member by providing both a spindle in the housing and a locking lip in the housing, forming a spindle recess in the fluid responsive member and a groove in the fluid responsive member and inserting the fluid responsive member into the housing to have the spindle engage the recess and the groove to engage the lip.

18. The method of claim 17 including forming the fluid responsive member with a plurality of vanes on a surface of the fluid responsive member between the spindle and the recess, and positioning the fluid responsive member in the housing such that the vanes contact the inlet fluid.

19. The method of claim 18 including forming the vanes on an exterior of the surface with vanes that taper in width from a wider top portion to a narrow bottom portion such that the wider portion of the vanes are oriented to face the inlet fluid and the narrow portion of the vanes address outlet fluid.

20. A dental prophy angle and drive mechanism, comprising, in combination:

a housing having a first end and a second end, a hand grasping area on an exterior of said housing and intermediate said first and second ends, a hollow passageway within an interior of said housing, entrance and exit means on said first end of said housing to couple respectively with a source of air to enter said housing and exhaust air to exit said housing, a partition within said housing to sequester entering air from exiting air, and air contacting means supported in said second end including prophy support means extending outside said housing, said air contacting means including a turbine having means to react to the air from said entrance means and divert this air to said exit means while imparting rotation to itself, and wherein said second end includes a turbine support means, said turbine support means including a socket on a top surface of said turbine and an annular groove on a side surface of said turbine, and said second end of said housing includes a complementally formed spindle for contact with said socket and said second end includes an annular lip for riding within said annular groove of said turbine to retain said turbine in said second end.

21. An integrally formed disposable dental handpiece drive mechanism and prophylaxis fitting, comprising, in combination:

a housing having a first end and a second end, an air coupling means at said first end, said second end of said housing supporting an output shaft emanating therefrom including means for attaching to said prophylaxis fitting, said output shaft including air reactive means including a turbine contained within said housing and in direct communication with air admitted by said air coupling means, whereby said output shaft is directly driven by air impinging thereagainst, and wherein said second end includes a turbine support means, said turbine support means including a socket on a top surface of said turbine and an annular groove on a side surface of said turbine, and said second end of said housing includes a complementally formed spindle for contact with said socket and said second end includes an annular lip for riding within said annular groove of said turbine to retain said turbine in said second end.

22. A method for rotating a prophylaxis instrument at speeds less than 50,000 rpm, the steps including;

forming a housing with a first end and a second end, configuring the housing with an interior partition extending from the first end to the second end, thereby defining an inlet flow path and an outlet flow path, coupling inlet fluid to the inlet flow path and an outlet fluid receiver to the outlet flow path, supporting and positioning a fluid responsive member in the second end of the housing to contact the inlet fluid and direct the fluid to the outlet flow path while reacting to the fluid flow by rotating, and utilizing the rotation of the fluid responsive member by coupling this fluid responsive member to an output device, and including supporting the fluid responsive member by providing both a spindle in the housing and a locking lip in the housing, forming a spindle recess in the fluid responsive member and a groove in the fluid responsive member and inserting the fluid responsive member into the housing to have the spindle engage the recess and the groove to engage the lip.

* * * * *